(12) United States Patent
Johnson

(10) Patent No.: US 6,297,227 B1
(45) Date of Patent: Oct. 2, 2001

(54) METHODS AND COMPOSITIONS FOR TREATING SINUSITIS, OTITIS MEDIA AND OTHER RELATED DISORDERS USING ANTIHISTAMINES

(75) Inventor: Nancy R. Johnson, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/391,797

(22) Filed: Sep. 9, 1999

Related U.S. Application Data

(60) Provisional application No. 60/099,681, filed on Sep. 10, 1998.

(51) Int. Cl.$^7$ ..................................................... A61K 31/58
(52) U.S. Cl. ............................................ 514/172; 514/169
(58) Field of Search ..................................... 514/170, 169, 514/172

(56) References Cited

U.S. PATENT DOCUMENTS

| | | |
|---|---|---|
| 4,472,393 | 9/1984 | Shapiro . |
| 4,731,477 | 3/1988 | Schumacher et al. . |
| 4,873,335 | 10/1989 | Schumacher et al. . |

OTHER PUBLICATIONS

*Conn's Current Therapy,* 235 (1997).
*Diseases of the Sinuses—A Comprehensive Textbook of Diagnosis and Treatment,* ed. M. E. Gershwin et al, Human Press, Totowa, New Jersey (1996), pp. 151–157.
*Allergy—Principles and Practice,* vol. II, ed. E. Middleton, Jr. et al, Mosby–Year Book, Inc., New York (1998), pp. 1027–1033.
Z. Pelikan, "The Role of Allergy in Sinus Disease", *Clinical Reviews in Allergy and Immunology* (1998) 16, 55–156.
J. Braun et al, *Allergy* (1997) 52 (6), 650–655.
Quercia et al, *Hosp. Formul.,* (1993) 28, 137–153.

*Primary Examiner*—Zohreh Fay

(57) ABSTRACT

The present invention discloses antibiotic-excluded compositions and methods to treat non-infective sinusitis and otitis media. The compositions comprise a therapeutically effective amount of a corticosteroid, and the methods comprise administering a pharmaceutical composition comprising a therapeutically effective amount of a corticosteroid. Preferred corticosteroids are mometasone furoate and mometasone furoate monohydrate.

8 Claims, No Drawings

METHODS AND COMPOSITIONS FOR TREATING SINUSITIS, OTITIS MEDIA AND OTHER RELATED DISORDERS USING ANTIHISTAMINES

This application claims benefit to provisional application No. 60/099,681 filed Sep. 10, 1998.

FIELD OF THE INVENTION

The present invention generally relates to methods of treating sinusitis and otitis media (including otitis media with effusion and persistent middle ear effusion) involving the administration of a therapeutically effective amount of a corticosteroid. It specifically relates to such treatment involving the administration of a therapeutically effective amount of mometasone furoate. The subject matter of this patent application is related to that disclosed in pending U.S. patent applications, Ser. No. 09/391,795 filed of even date herewith, Ser. No. 08/376,506, filed Jan. 23, 1995, and Ser. No. 07/984,573, filed Apr. 29, 1998.

BACKGROUND OF THE INVENTION

Sinusitis is the most frequently reported chronic disease in the United States, affecting more than 14% of the population. Sinusitis is an inflammation of the mucosa of the paranasal sinuses. Generally, there is an allergic cause to sinusitis. Otitis media, like sinusitis, is also generally considered to have an allergic cause. These are also characterized by retention of thickened respiratory secretions; however, the inflammation is manifest in the ear rather than in the sinuses. A discussion of sinusitis and otitis media can be found in Conn's Current Therapy, 235 (1997); *Diseases of the Sinuses—A Comprehensive Textbook of Diagnosis and Treatment*, ed. M. E. Gershwin et al, Human Press, Totowa, N.J., pages 151–157 (1996); and *Allergy—Principles and Practice*, Volume II, ed. E. Middleton, Jr. et al, Mosby-Year Book, Inc., New York, pages 1027–1033 (1998). Also, a review of sinusitis and related facts is given by Z. Pelikan, "The Role of Allergy in Sinus Disease", *Clinical Reviews in Allergy and Immunology*, 16, 55–156 (1998).

Sinusitis and otitis media are often typically treated as infectious diseases. The treatment typically includes administration of an antibiotic along with a corticosteroid and an antihistamine, or a nasal decongestant. such as described in, for example, J. Braun et al, *Allergy*, 52 (6) 650–655 (1997). There are, however, occasions, when the sinusitis or otitis media is not necessarily accompanied by an infection. This is particularly true when the disease is associated with allergic rhinitis. At those times, administration of an antibiotic may not be needed. Physicians, however, do not generally administer corticosteroids for these indications without accompanying antibiotic.

Certain corticosteroids, e.g., beclomethasone dipropionate, are commercially available for the treatment of diseases such as rhinitis and bronchial asthma. However, the art does not teach the utility of a corticosteroid as substantially a main component in the treatment of non-infective sinusitis or otitis media in the absence of antibiotics.

It would be desirable to find methods of treatment for non-infective sinusitis or otitis media using an effective amount of substantially a corticosteroid as an active ingredient in the absence of antibiotics.

It would also be desirable to find a corticosteroid which is therapeutically effective in treating sinusitis and otitis media and which also exhibits low bioavailability and low systemic side-effects when it is administered intra-nasally or by oral inhalation.

Other desires, objectives and advantages of the present invention will be apparent to those skilled in the art from the accompanying description and claims.

SUMMARY OF THE INVENTION

The above-noted objectives are addressed by the present invention which, in one embodiment, provides methods and pharmaceutical compositions for the treatment of non-infectious sinusitis and otitis media. The composition comprises a therapeutically effective amount of one or more corticosteroids or a pharmaceutically acceptable derivative of such corticosteroid(s). Additionally, a pharmaceutically acceptable carrier may be optionally present in the inventive composition. While still additional ingredient or ingredients may optionally be present, the corticosteroid(s) is (are) the major active ingredient(s) in the composition. Antibiotics, however, are absent in the composition. Preferred corticosteroids useful in the practice of the present invention are mometasone furoate (also known as SCH 32088) as well mometasone furoate monohydrate.

The present invention additionally discloses a method for the treatment of non-infectious sinusitis and otitis media or both in a mammalian organism in need of such treatment, such treatment comprising administering a pharmaceutical composition described above.

The present invention provides a method of treating non-infective sinusitis and otitis media or both in patients afflicted with that disease or diseases, which method comprises administering at least once-a-day to said patients a substantially non-systematically bio-available amount of a corticosteroid effective for treating said disease.

In an aspect of the present invention, there is provided a method of treating non-infective sinusitis and otitis media or both in patients afflicted with that disease or diseases which method comprises administering at least once-a-day to said patients an amount of a corticosteroid effective to maximize treating said sinusitis or otitis media while simultaneously substantially minimizing systemic absorption thereof.

In another aspect of the present invention, there is provided a method of treating non-infective sinusitis or otitis media or both in patients afflicted with said disease or diseases which method comprises administering at least once-a-day, via oral inhalation or nasal ingestion, to said patients an amount of a corticosteroid effective to maximize topically treating said disease while simultaneously substantially minimizing the systemic absorption thereof.

In yet another aspect of the present invention, there is provided a method of treating non-infective sinusitis or otitis media or both in patients afflicted with said disease(s) which method comprises administering at least once-a-day, via oral inhalation or nasal ingestion, to said patients an amount of mometasone furoate effective to maximize topically treating said disease while simultaneously substantially minimizing the systemic absorption thereof.

In a still another aspect of the present invention, there is provided a method of treating non-infective sinusitis or otitis media or both in patients afflicted with said disease(s) which method comprises administering at least once-a-day, via oral inhalation or nasal ingestion, to said patients an amount of mometasone furoate monohydrate effective to maximize topically treating said disease while simultaneously substantially minimizing the systemic absorption thereof.

DESCRIPTION OF THE INVENTION

In one embodiment, this invention provides pharmaceutical compositions for the treatment of non-infectious sinusitis and otitis media. The term "otitis media" also includes otitis media with effusion and persistent middle ear effusion in this invention. The composition comprises a therapeutically effective amount of one or more corticosteroid or a pharmaceutically acceptable derivative of such corticosteroid, optionally in combination with a pharmaceutically acceptable carrier. While further additional ingredients may optionally be present, the corticosteroid is the major active ingredient in the composition. Antibiotics, however, are absent in the composition.

While several corticosteroids may be useful in the practice of this invention, preferred corticosteroids are mometasone furoate and mometasone furoate monohydrate. Mometasone furoate, which is 9α,21-dichloro-16α-methyl-1,4-pregnadiene-11β, 17α-diol-3,20-dione-17-(2'-furoate), is a corticosteroid approved for topical dermatologic use to treat inflammatory and/or pruritic manifestations of corticosteroid-responsive dermatoses. Mometasone furoate may be prepared in accordance with the procedures disclosed in U.S. Pat. Nos. 4,472,393, 4,731,447, and 4,873, 335. Mometasone furoate monohydrate is disclosed in the afore-mentioned U.S. patent application, Ser. No. 07/984, 573, filed Apr. 29, 1998.

In a further embodiment, this invention discloses a method for the treatment of non-infectious sinusitis and otitis media or both in a mammalian organism in need of such treatment, such treatment comprising administering a pharmaceutical composition described above.

When mometasone furoate or its monohydrate is administered orally (i.e., swallowed as an oral suspension) or by oral or nasal inhalation, there is a substantial absence of absorption systemically into the bloodstream of mometasone furoate i.e., there is essentially no parent drug (substantially less than 1% of mometasone furoate) which reaches the bloodstream from the gastro-intestinal tract. Any mometasone furoate found in the bloodstream after it has been administered by oral or nasal inhalation has already passed through the lungs and/or airway passage tissue. Therefore, there is no "wasted" drug (i.e., drug that reaches the relevant tissue in the lungs and/or airways only via the bloodstream). Thus, mometasone furoate is an ideal drug for treating diseases such as sinusitis or otitis media.

The mometasone furoate or its monohydrate administered, for example, by oral inhalation or intranasally to treat sinusitis or otitis media may be used as monotherapy or as adjuvant therapy with for example cromolyn sodium or nedocromil sodium (available from Fisons); immunosuppressive agents such as methotrexate sodium (available from Astra Pharmaceutical Products, Inc.), oral gold, or cyclosporine A (available from Novartis Pharmaceuticals under the SANDIMMUNE® tradename); bronchodilators such as albuterol (available from Schering Corporation under the PROVENTIL® tradename) or theophylline (available from Key Pharmaceuticals of Schering Corporation under the Theo-Dur® tradename).

The devices useful for providing measured substantially non-systematically bioavailable amounts of aerosolized mometasone furoate or its monohydrate or aerosolized pharmaceutical compositions thereof for delivery to the affected patients by oral inhalation or intranasal inhalation include pressurized metered-dose inhalers ("MDI") which deliver aerosolized particles or droplets or similar forms suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents; dry-powder inhalers either breath activated or delivered by air or gas pressure such as the dry-powder inhaler disclosed in the Schering Corporation International Patent Application No. PCT/US92/05225, published Jan. 7, 1993 as well as the TURBUHALER™ (available from Astra Pharmaceutical Products, Inc.) or the ROTAHALER™ (available from Allen & Hanburys) which may be used to deliver the aerosolized mometasone furoate as a finely milled powder in large aggregates either alone or in combination with some pharmaceutically acceptable carrier e.g. lactose, and nebulizers. The inhalation of aerosolized drugs by use of nebulizers and metered-dose inhalers such as used to deliver VANCENASE® (brand of beclomethasone dipropionate) inhalation aerosol (available from Schering Corporation, Kenilworth, N.J.) is disclosed in Remington's Pharmaceutical Sciences, Mack Publishing Co. Easton Pa., 15th Ed. Chapter 99, pages 1910–1912.

Mometasone furoate or its monohydrate may also be administered in specific, measured amounts in the form of an aqueous suspension by use of a pump spray bottle such as the bottles used to deliver VANCENASE AQ® Nasal Spray as well as the spray bottle disclosed in the Schering Corporation Industrial Design Deposit DM/026304, registered by the Hague Union on Jun. 1, 1993 (each are available from Schering Corporation). The aqueous suspensions of the present invention may be prepared by admixing mometasone furoate or mometasone furoate monohydrate (preferably mometasone furoate monohydrate) with water and other pharmaceutically acceptable excipients. The aqueous suspensions may contain from about 0.01 to 10.0 mg, preferably 0.1 to 10.0 mg of mometasone furoate monohydrate per gram of suspension. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

Based on the judgment of the attending clinician, the amount of mometasone furoate or its monohydrate administered and the treatment regimen used will, of course, be dependent on the age, sex and medical history of the patient being treated, the severity of the specific disease condition and the tolerance of patient to the treatment regimen.

In treating sinusitis or otitis media, the aqueous suspension of mometasone furoate or its monohydrate may be administered intranasally by inserting an appropriate device (such as the pump spray bottle used to deliver VANCENASE AQ® Nasal Spray as well as the spray bottle disclosed in the Schering Corporation Industrial Design Deposit DM/026304 registered Jun. 1, 1993) into each nostril. Active drug is then expelled (nasal spray device) or could be nasally inhaled (sniffed) as a powder.

As stated earlier, a pharmaceutically acceptable carrier may also be present in the composition. The carrier is suitably selected with respect to the intended form of administration, and consistent with conventional pharmaceutical practices. Such techniques are well known to those skilled in the art.

The term "dosage form" herein refers to a composition containing the corticosteroid and any optional ingredients formulated into a delivery system.

The corticosteroid and any optional ingredient or ingredients may be administered in combination or separately in the method of treating the non-infective sinusitis or otitis media. For example, they may be administered concurrently or sequentially, i.e. they may be administered in combination either concurrently or by the sequential administration of the ingredients in a suitable order.

The phrase "therapeutically effective amount" means that amount of the corticosteroid which provides a therapeutical benefit in the treatment or management of the non-infective sinusitis or otitis media.

The magnitude of a therapeutic dose of the corticosteroid in the acute or chronic management of the targeted disease or condition will vary with the severity of the condition to be treated and the route of administration. The dose is typically 0.01 to 10.0 mg per dosage. The dose, and perhaps the dose frequency, will also vary according the age, body weight, and response of the individual patient. Suitable total daily dose ranges can be readily determined by those skilled in the art. It is further recommended that children, patients aged over 65 years, and those with impaired renal or haptic function initially receive low doses. Further, it is noted that the clinician or treating physician will know how and when to adjust, interrupt, or terminate therapy in conjunction with individual patient response.

Pharmaceutical compositions for use in the methods of the present invention may be prepared by any of the methods of pharmacy, but all methods include the step of bringing into association the corticosteroid and any optional ingredient or ingredients. In general, the compositions are prepared by uniformly and intimately admixing the corticosteroid with any other ingredients.

Various modifications of the invention in addition to those shown and described herein will be apparent to those skilled in the art from the forgoing description. Such modifications are also intended to fall within the scope of the appended claims.

What is claimed is:

1. A method of treating sinusitis in patients afflicted with same, which method comprises administering at least once-a-day to said patients a substantially non-systematically bioavailable amount of a corticosteroid effective for treating said disease.

2. The method of claim 1, wherein said corticosteroid is mometasone furoate.

3. The method of claim 1, wherein said corticosteroid is mometasone furoate monohydrate.

4. The method of claim 1, wherein said administered is administered as an aqueous suspension.

5. The method of claim 1, wherein said corticosteroid is administered as an intranasal inhalant.

6. The method of claim 1, wherein said administration is performed orally.

7. The method of claim 6 wherein a metered dose inhaler is used to administer the corticosteroid.

8. The method of claim 6 wherein a dry powder inhaler is used to administer the corticosteroid.

* * * * *

UNITED STATES PATENT AND TRADEMARK OFFICE
CERTIFICATE OF CORRECTION

PATENT NO.   : 6,297,227 B1
DATED        : October 2, 2001
INVENTOR(S)  : N. Johnson Page 1 of 1

It is certified that error appears in the above-identified patent and that said Letters Patent is hereby corrected as shown below:

<u>Title page,</u>
Item [54], Title, delete "ANTIHISTAMINES" and insert -- CORTICOSTEROIDS -- therefor.
Item [74], insert -- *Attorney, Agent or Firm*: Palaiyur S. Kalyanaraman --

Signed and Sealed this

Twenty-eighth Day of May, 2002

Attest:

JAMES E. ROGAN
*Attesting Officer*   *Director of the United States Patent and Trademark Office*